(12) United States Patent
Johnson et al.

(10) Patent No.: US 11,992,380 B2
(45) Date of Patent: May 28, 2024

(54) SYSTEM AND METHOD FOR PROVIDING A PEDIATRIC CROWN

(71) Applicants: Andrew C. Johnson, Fayetteville, AR (US); Charles A. Davis, Jr., Tuscon, AZ (US)

(72) Inventors: Andrew C. Johnson, Fayetteville, AR (US); Charles A. Davis, Jr., Tuscon, AZ (US)

(73) Assignee: Alphabyte LLC, Tucson, AZ (US)

( * ) Notice: Subject to any disclaimer, the term of this patent is extended or adjusted under 35 U.S.C. 154(b) by 510 days.

(21) Appl. No.: 17/320,335

(22) Filed: May 14, 2021

(65) Prior Publication Data

US 2024/0099810 A1    Mar. 28, 2024

Related U.S. Application Data

(60) Provisional application No. 63/026,922, filed on May 19, 2020.

(51) Int. Cl.

| | |
|---|---|
| *A61C 13/107* | (2006.01) |
| *A61C 5/70* | (2017.01) |
| *A61C 13/08* | (2006.01) |
| *G06F 3/00* | (2006.01) |
| *G06Q 10/087* | (2023.01) |
| *G06T 1/00* | (2006.01) |
| *G06T 7/62* | (2017.01) |
| *A61C 19/10* | (2006.01) |

(52) U.S. Cl.
CPC .............. *A61C 5/70* (2017.02); *A61C 13/082* (2013.01); *G06F 3/00* (2013.01); *G06Q 10/087* (2013.01); *G06T 1/00* (2013.01); *G06T 1/0007* (2013.01); *G06T 7/62* (2017.01); *A61C 19/10* (2013.01); *G06T 2207/30036* (2013.01)

(58) Field of Classification Search
CPC .......... A61C 5/70; A61C 13/082; G06T 7/62; G06T 1/00; G06T 1/0007; G06F 3/00; G06Q 10/087
See application file for complete search history.

(56) References Cited

U.S. PATENT DOCUMENTS

| | | | |
|---|---|---|---|
| 8,545,221 B2 * | 10/2013 | Stone-Collonge | A61C 7/08 433/24 |
| 2006/0008777 A1 * | 1/2006 | Peterson | A61C 13/0019 433/223 |
| 2015/0111177 A1 * | 4/2015 | Fisker | A61C 9/004 433/199.1 |

(Continued)

*Primary Examiner* — Mohammed H Zuberi
(74) *Attorney, Agent, or Firm* — Wright Lindsey Jennings, LLP; Meredith Lowry (57) ABSTRACT

A system and method and system for providing preoperative patient intraoral scanning for diagnosis and preparation of a treatment plan utilizing the proposed system in advance of the crown surgery and intraoperative patient intraoral scanning for system assessment and verification for the method of treatment. More specifically, the proposed invention proposes a method and system of patient intraoral scanning to identify the best prefabricated crown for use for the patient and develop a plan for intraoral surface treatment for the identified prefabricated crown and automated crown inventory management.

11 Claims, 7 Drawing Sheets
(1 of 7 Drawing Sheet(s) Filed in Color)

(56) References Cited

U.S. PATENT DOCUMENTS

| | | | |
|---|---|---|---|
| 2015/0245886 A1* | 9/2015 | Hegland | A61C 13/0003 |
| | | | 433/29 |
| 2018/0036097 A1* | 2/2018 | Kim | A61C 1/082 |
| 2019/0021815 A1* | 1/2019 | Herrmann | A61C 5/73 |
| 2019/0209274 A1* | 7/2019 | Barak | A61C 5/007 |
| 2020/0206092 A1* | 7/2020 | Herrmann | A61K 6/887 |
| 2022/0000582 A1* | 1/2022 | Ziskind | A61C 5/77 |
| 2022/0092999 A1* | 3/2022 | Callan | G09B 19/0084 |
| 2022/0096205 A1* | 3/2022 | Prasad | A61C 5/77 |
| 2023/0084657 A1* | 3/2023 | Kim | A61C 5/77 |
| | | | 433/222.1 |

* cited by examiner

SYSTEM AND METHOD FOR PROVIDING A PEDIATRIC CROWN

CROSS-REFERENCE TO RELATED APPLICATIONS

This application claims priority to and is a continuation-in-part of U.S. application Serial No. U.S. application 63/026,922, filed May 19, 2020, the entirety of which is hereby incorporated by reference.

STATEMENT REGARDING FEDERALLY SPONSORED RESEARCH OR DEVELOPMENT

Not applicable.

BACKGROUND OF THE INVENTION

The invention is related generally to the field of pediatric dentistry, but allows similar applications in general dentistry and prosthodontics as well. More particularly, the present invention is related to a method and system for providing and facilitating placement of a prefabricated crown.

BRIEF SUMMARY OF THE INVENTION

The process for obtaining a crown to repair a typical adult human tooth is drastically different than the process for repairing a juvenile or child tooth with a crown. Crowns used to repair adult human teeth are usually custom fabricated according to a mold of a tooth being repaired which is provided by the dental practitioner or through digital scanning. These custom fabricated crowns may be formed of various metals or ceramics or some combination of materials. While many custom dental crowns are still fabricated by hand, many are now created digitally. Using the practitioner-provided mold as a guide, computer software, through a CAD/CAM technology, directs a milling machine or a 3d printer to mill or print a coping or framework of the crown or even the entire crown structure out of the chosen material, such as metal or ceramic. This work results in a crown that resembles aesthetically a human tooth that fits accurately in the adult mouth.

Although aesthetically-pleasing and precise in fit, the patient receiving such a crown must make multiple visits to the dental office to achieve this result and the process is time-consuming and expensive. Given the time and the cost, this process is undesirable for a child patient, when the tooth being replaced is a child's (baby) tooth which will eventually be lost and replaced by permanent teeth through the natural maturing process. Instead, dentists have developed prefabricated crowns that do not require molds and multiple visits to the dentist. The use of prefabricated, stainless steel crowns for restoring badly broken-down children's teeth is now the standard of care in pediatric dentistry. The American Academy of Pediatric Dentists has encouraged crown restorations due to the poor outcomes resulting from the use of fillings in certain high-risk groups, especially children with the inability to cooperate in the dental chair, thereby necessitating the use of general anesthesia for their dental treatment. Prefabricated crowns are a very efficient and reliable restoration resource and are the restoration of choice in teeth with moderate to severe dental decay.

Stainless steel prefabricated crowns are the most versatile and widely used crowns in pediatric dentistry. However, due to their unaesthetic appearance, many parents request that the dentist use preformed zirconia ceramic crowns for a more aesthetic option for their patients. These new crowns, such as Kinder Krowns are more enamel-like in appearance but thicker and less flexible that the stainless steel prefabricated crowns. Although these new crowns are much more aesthetically pleasing than the all-stainless-steel crowns, they came with some significant drawbacks.

While the main benefit of the zirconia crowns was their more aesthetic appearance compared to their stainless steel predecessors, they also demonstrate better wear resistance over time and facilitate good soft tissue health in the peripheral gum line. This new product, however, requires a new method for preparing the tooth and seating the crowns. The nature of the rigid zirconia crowns made it such that if the tooth was prepared inadequately, the zirconia crown would not seat properly and/or crack. Therefore, it was recommended that these restorations have a passive fit to the tooth, minimizing the potential to crack the zirconia. This requires that the dentist must spend additional time more aggressively preparing the underlying tooth to ensure that the zirconia crown will fit appropriately or risk that the zirconia crown might crack. This increases the total procedure time as well as any associated sedation time. Additionally, lengthier procedures as well as any cracking of the zirconia requiring replacement is a potential loss of revenue to the dentist.

An additional drawback of the prefabricated zirconia crowns is the increased inventory of crowns required to be maintained by a pediatric dentist. Because the prefabricated zirconia crowns are typically much more costly per unit and so many more crown try-ins are required to achieve proper fit, the cost of accomplishing the average zirconia crown versus the average stainless steel crown in pediatric applications is significantly higher.

The proposed invention changes this system by providing a method and system for providing preoperative patient intraoral scanning for diagnosis and preparation of a treatment plan utilizing the proposed system in advance of the crown surgery and/or intraoperative patient intraoral scanning for system assessment, restoration selection and verification for the method of treatment as well as post-treatment crown inventory replenishment. More specifically, the proposed invention proposes a method and system of patient intraoral scanning to identify the best prefabricated crown for use for the patient and develop a plan for intraoral surface treatment which compliments the identified prefabricated crown.

The proposed invention proposes to increase the safety of the pediatric crown placement by better controlling the required tooth preparation, reducing the procedure time for the patient and the sedation time of the patient. Another objective of the present invention is to reduce risks to the patient by lessening the amount of crown try-ins for the patient and need for resterilization of crowns tried-in and rejected, which reduces the aspiration risk and the disease transmission risks to the patient. By utilizing a digital intraoral scan for the tooth, the risk of choking on the impression material needed to fit the crown is lessened. Another objective of the present invention is to minimize overpreparation of the tooth, which lessens pulpal involvement and shortens the procedure time and mitigates postoperative complications like sensitivity and infections.

Another objective of the proposed invention is the increased efficiencies to the doctor and patient. The shortened procedure time necessary allows the patient and the doctor to have more time in their respective lives. The more information about the patient's mouth and tooth provided by the system allows the dentist to know more accurately the crown size for placement and reduces the need to have a large inventory of crowns at all times, perhaps down to only needing the one pre-selected crown on-hand. Finally, the present system allows a more successful placement of the crown, reducing the need to fallback to a stainless steel crown if the zirconia crown attempt fails.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Generally speaking, the present invention is directed to a system 10 and method 4 for providing preoperative patient intraoral scanning for diagnosis and preparation of a treatment plan utilizing the proposed system in advance of the crown surgery and intraoperative patient intraoral scanning for system assessment and verification for the method of treatment. More specifically, the proposed invention proposes a method 4 and system 10 of patient digital scanning to identify the best prefabricated crown for use for the patient and develop a plan for intraoral surface treatment for the identified prefabricated crown and then automates the reorder of the selected pediatric crown for the inventory. The proposed invention may additionally provide a method 4 and system 10 of digitally scanning of a model from a traditional impression as a means of secondarily digitizing the tooth anatomy and running the digital crown selection algorithms.

"Artificial intelligence" as used herein to broadly describe any computationally intelligent systems that combine knowledge, techniques, and methodologies. An Al engine may be any system configured to apply knowledge and that can adapt itself and learn to do better in changing environments. Thus, the Al engine may employ any one or combination of the following computational techniques: neural network, constraint program, fuzzy logic, classification, conventional artificial intelligence, symbolic manipulation, fuzzy set theory, evolutionary computation, cybernetics, data mining, approximate reasoning, derivative-free optimization, decision trees, and/or soft computing. Employing any computationally intelligent techniques, the Al engine may learn to adapt to unknown and/or changing environment for better performance.

As used herein, the term "computing device," refers to a device including at least one processor, memory and having computing capabilities. Some examples of a computing device include a PC, laptop, tablet, or a smartphone having a display. In this example implementation, the computing device (CPU) may be coupled, connected, and/or in communication with a network via communication channels including, but not limited to Internet connections, satellite communications, wireless channels, cloud connections, etc.

As used herein, the term database refers to an organized collection of data with a software system designed to allow the definition, creation, querying, update, and administration of databases.

The term patient encompasses, but is not limited to, a recipient of health care services.

As used herein, the term platform refers to a computer software application hosted on a server, stored persistently on storage or memory available to the server, and executing on one or more computing devices of the server.

As used herein, the term server refers to a system (software and suitable computer hardware) that responds to requests across a computer network.

The network represents the communication pathway between computing devices 12 and the online system stored on one or more servers. In one embodiment, the network is the internet. The network can also utilize dedicated or private communication links (e.g. WAN, MAN, or LAN) that are not necessarily part of the Internet. The networked patient devices 12 use standard communication technologies and/or protocols.

Figure 1:
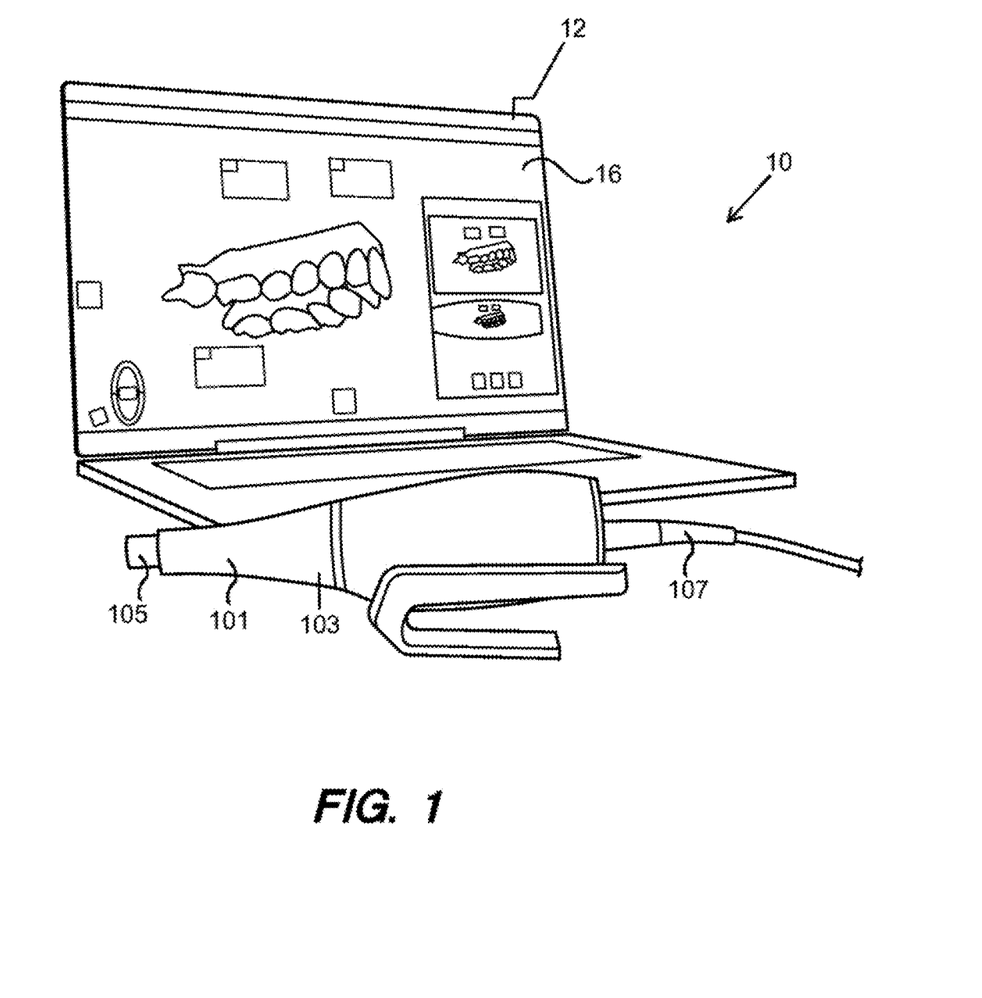
FIG. 1 is a front view of the system of the present invention.

FIG. 1 is a front view of the system 10 of the present invention showing a representative computing device 12 having a data processing system, which may include hardware, software, and/or firmware for performing many of these steps described below and housing the online platform system 10 to identify the best prefabricated crown for use for the patient and develop a plan for intraoral surface treatment for the identified prefabricated crown. The device 12 executes an operating system, for example, a Microsoft Windows-compatible operating system (OS), Apple OS X or iOS, a Linux distribution, or Google's Android OS. In some embodiments, the device 12 may use a web browser, such as Microsoft Internet Explorer, Mozilla Firefox, Google Chrome, Apple Safari and/or Opera, as an interface to interact with the platform either through software or online access. In other embodiment, the device 12 can execute a dedicated application for accessing the platform 10 to show the user interface of the platform. As shown in FIG. 1, the user interface provides a three-dimensional display of a pediatric patient's teeth as captured by the intraoral scanner 101 of the system 10 and a various menus and tools that will be discussed further below.

The data processing system typically includes at least one processor which communicates with a number of peripheral devices. These peripheral devices typically include a storage subsystem (memory and file storage), a set of user interface input and output devices, and an interface to outside networks, including the Internet. The user interface input devices may include a keyboard and may further include a pointing device and a scanner 101.

User interface output devices may include a printer and a display system, which includes a display controller and a display device 16 coupled to the controller. The display device 16 may be a flat-panel device such as a liquid crystal display (LCD), or a projection device.

The storage system may maintain the basic programming and data constructs that provide the functionality of the present invention. The methods described herein may be configured as software, firmware and/or hardware, and (of software/firmware) may be stored in storage system. The storage system typically comprises memory and file systems. The memory system typically includes a number of memories including a main random access memory (RAM) for storage of instructions and data during program execution and a read only memory (ROM) in which fixed instructions are stored. In the case of Macintosh-compatible personal computers the ROM would include portions of the operating system; in the case of IBM-compatible personal computers, this would include the BIOS (basic input/output system). The file storage system may provide persistent (nonvolatile) storage for program and data files, and may include at least one hard disk drive or more drives located at a remote location, such as in a server on a local area network or at a site on the Internet. With the exception of the scanner 101, the other input devices, and the display, the other components need not be at the same physical location. For example, the file storage system could be connected over various local-area or wide-area network server.

The storage system contains an inventory database or file storage of a multitude of prefabricated or preformed crown potentials for placement in the mouth of a patient. The inventory database provides the characteristics for the pediatric crown potentials, size, type of tooth, color of preferred crown, universal, midsize or fullsize, narrow or wide, and left, right or both, and interior crown shape and size to allow for artificial intelligence to select the appropriate tooth based on desired characteristics of the pediatric crown or for the user to narrow the potential inventory.

As shown in FIG. 1, an intraoral scanner 101 may be configured or adapted as described herein to generate 3D models having both surface and internal features. As shown FIG. 1, an exemplary intraoral scanner may include a wand 103 that can be hand-held by an operator (e.g., dentist, dental hygienist, technician, etc.) and moved over a subject's tooth or teeth to scan both surface and internal structures. The wand may include one or more sensors 105 (e.g., cameras such as CMOS, CCDs, detectors, etc.) and one or more light sources configured to emit light in a first spectral range for detection of surface features (e.g., visible light, monochromatic visible light, etc), a second color light source (e.g., white light between 400-700 nm, e.g., approximately 400-600 nm), and a third light source configured to emit light in a second spectral range for detection of internal features within the tooth (e.g., by trans-illumination, small-angle penetration imaging, laser florescence, etc., which may generically be referred to as penetration imaging, e.g., in the near-IR). The light source may be any appropriate light source, including LED, fiber optic, etc. The wand 103 may include one or more controls (buttons, switching, dials, touchscreens, etc.) to aid in control (e.g., turning the wand on/of, etc.); alternatively or additionally, one or more controls, not shown, may be present on other parts of the intraoral scanner.

The intraoral scanner 101 may also include one or more processors, including linked processors or remote processors, for both controlling the wand 103 operation, including coordinating the scanning and in reviewing and processing the scanning and generation of the 3D model including surface and internal features. The one or more processors may include or may be coupled with a memory for storing scanned data (surface data, internal feature data, etc.). As shown in FIG. 1, communications circuitry and connections 107, including wireless or wired communications circuitry may also be included for communicating with components of the system (including the wand) or external components, including external processors. For example the system 10 may be configured to send and receive scans or 3D models from the scanner 101. One or more additional outputs may also be included for outputting or presenting information, including display screens, printers, etc. As mentioned, inputs (buttons, touchscreens, etc.) may be included and the apparatus may allow or request user input for controlling scanning and other operations.

Figure 2:
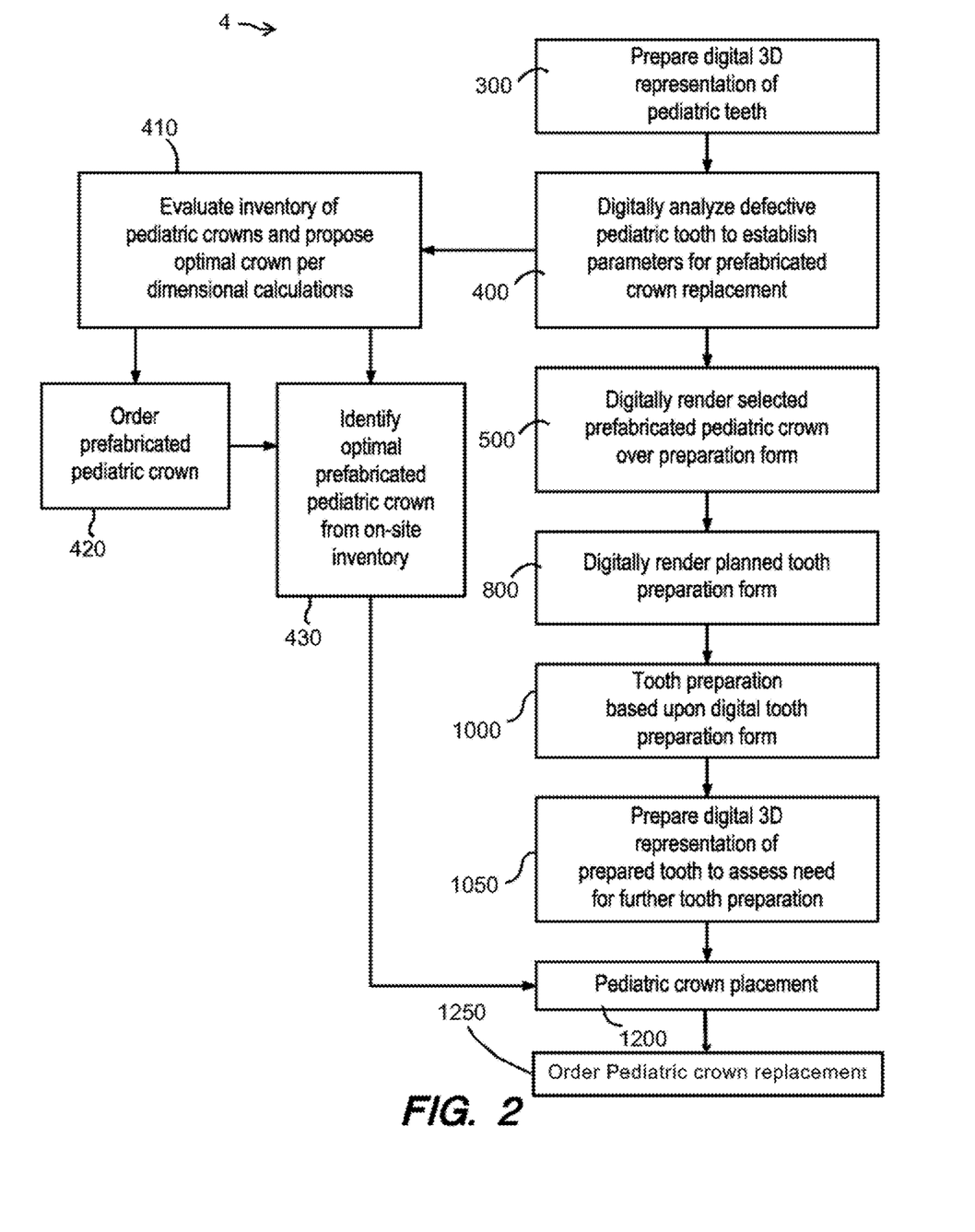
FIG. 2 is a schematic of the method of the present invention.

The method 4 of the present invention will be first described with later attention to the illustrations of the method in the subsequent figures. FIG. 2 is a schematic of the method 4 of the present invention that outlines the steps for the present invention. As illustrated, a user of the present invention utilizes the intraoral scanner 101 shown in FIG. 1 and the computing device 12 to prepare 300 a digital three-dimensional (3D) representation of a pediatric patient's teeth 304 and the affected tooth 302, as reflected in FIG. 3. The defective tooth is digitally removed 400 to provide an empty cavity space 402 to allow the platform to analyze the space 402 and evaluate 410 the library of prefabricated crown dimensions by digital cross-referencing to provide an optimal crown based on the dimensional calculations and a menu 404 of acceptable crown choices for view and selection as shown in FIG. 4. The system 10 is configured to access and evaluate the inventory of the prefabricated crowns in the system databases and file storage of the system 10 storage system. The identification 430 of suitable prefabricated crowns in the system may utilize artificial intelligence or provide the user with suitable prefabricated crowns based upon a classification system using a variety of characteristics 403, including current availability, size, brand/manufacturer, material, type of tooth, and color of preferred crown. As shown, the user of the platform 10 can view the characteristics 403 of the prefabricated crowns in the inventory 404 shown in the platform 10 and make digital selections of the prefabricated crowns to fit within the digitally removed defected tooth space 402. In the event that the optimal crown is unavailable, the system 10 allows the user to order 420 the prefabricated pediatric crown.

Figure 5:
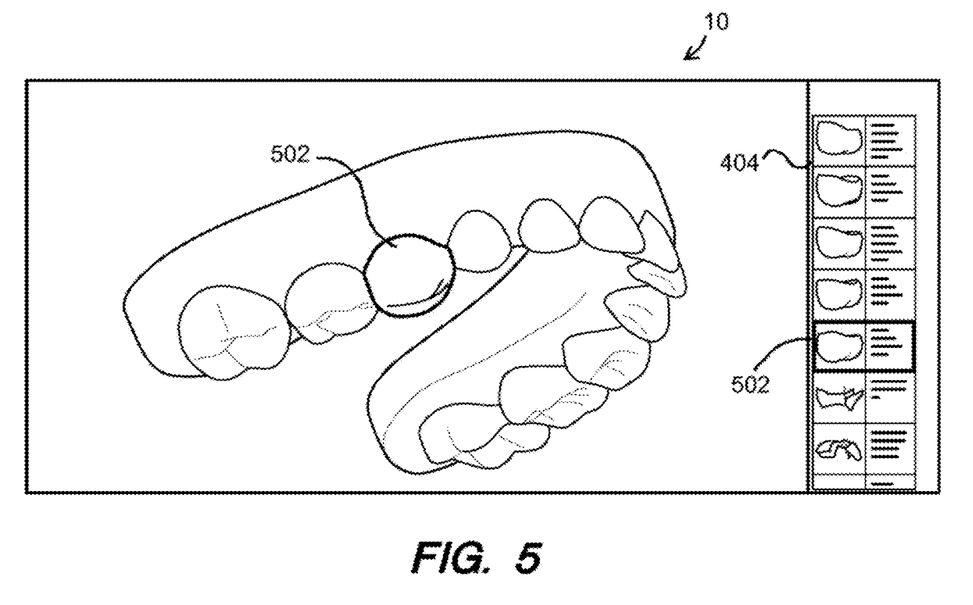
FIG. 5 is a digital image created by the present invention showing the digital placement of a potential crown drawn from the database system of the present invention demonstrating a resulting misfit because the virtual crown selected is too large.
Figure 6:
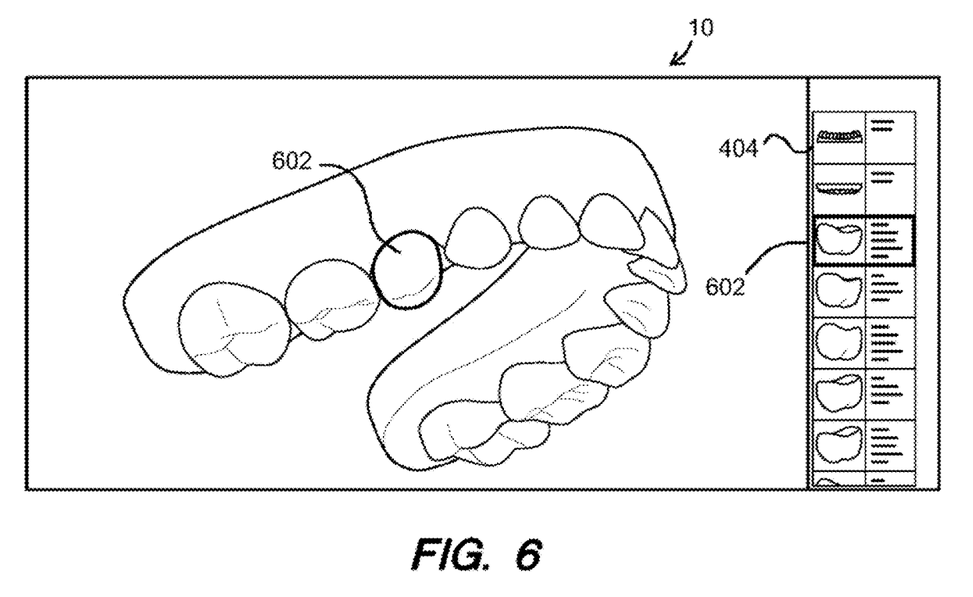
FIG. 6 is a digital image created by the present invention showing the virtual placement of a potential crown drawn from the database system of the present invention demonstrating a resulting misfit because the virtual crown selected is too small.
Figure 7:
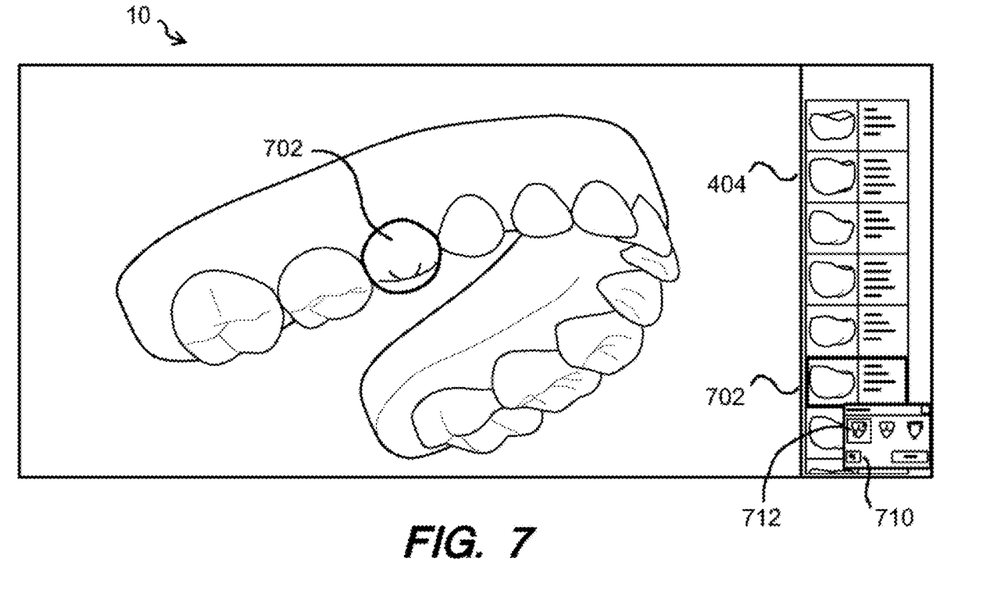
FIG. 7 is a digital image created by the present invention showing the digital placement of a potential crown drawn from the database system of the present invention demonstrating a good fit because the virtual crown dimensions are optimal.

This process of evaluating the inventory of pediatric crowns to determine appropriate fit is shown through the images in FIGS. 5-7. As illustrated digitally, a user of the platform 10 can select the fit of the available pediatric crowns and the system will digitally render 500 the selected pediatric crown 502 into the empty space 402.

As shown in the schematic of the method 4 in FIG. 2, once the appropriate prefabricated crown is selected 500, the system 10 provides the user with current inventory information and the opportunity to order 420 the prefabricated pediatric crown from the supplier if the crown is not in the current inventory. Once acquired, the prefabricated pediatric crown is prepared for intraoral placement.

Figure 8:
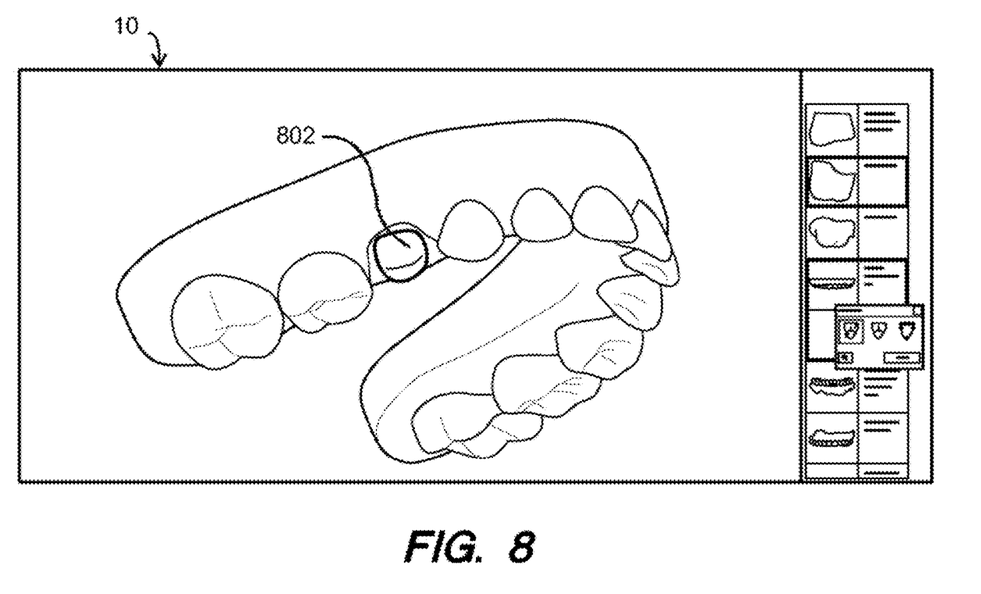
FIG. 8 is a digital image created by the present invention showing a digital form for the tooth preparation of the affected tooth extrapolated from the known interior dimensions of the optimal virtual crown.
Figure 9:
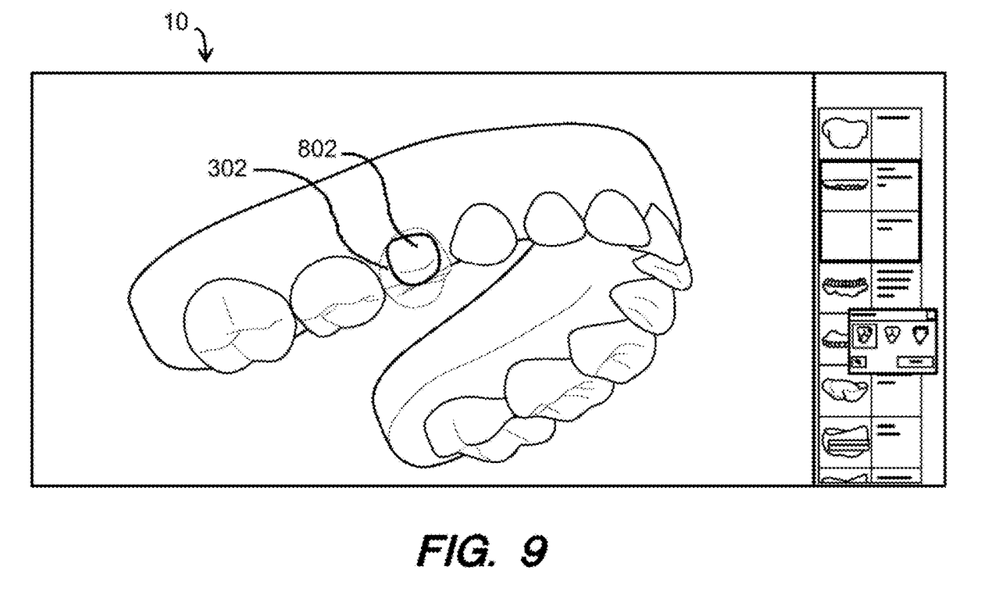
FIG. 9 is a digital image created by the present invention showing the affected tooth contours superimposed on the tooth preparation form required for fitting the optimal virtual crown.

As shown in FIG. 2 and illustrated in FIG. 8, the system 10 digitally renders 800 an ideal tooth preparation form 802 extrapolated from the selected virtual crown. This digital rendering can be performed utilizing artificial intelligence, the user, or a combination of both. The selected prefabricated pediatric crown is then digitally rendered over the preparation form, as shown in FIG. 9.

Figure 10:
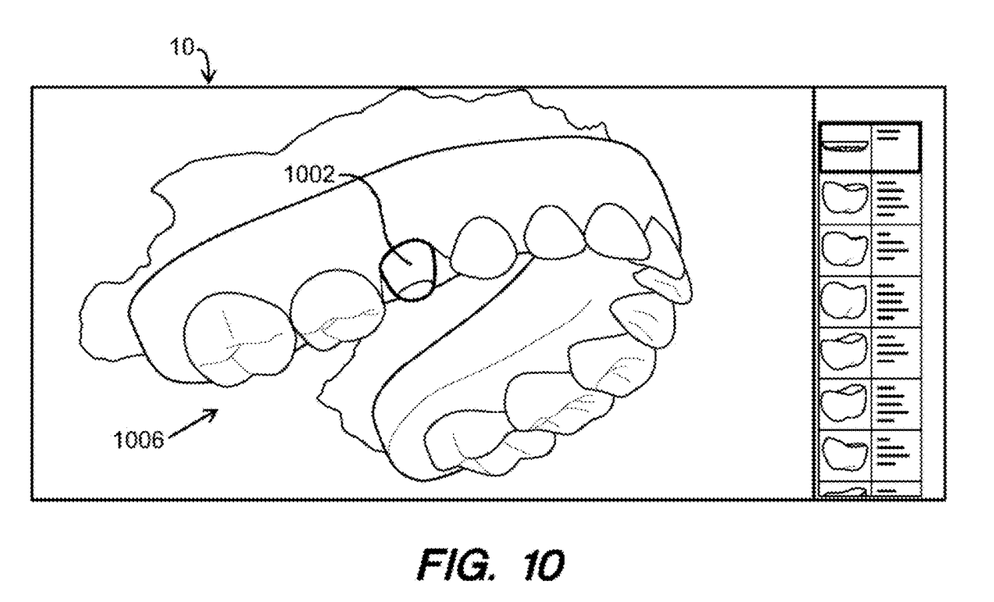
FIG. 10 is a digital image created by the present invention showing an initial tooth preparation of the affected tooth.
Figure 11:
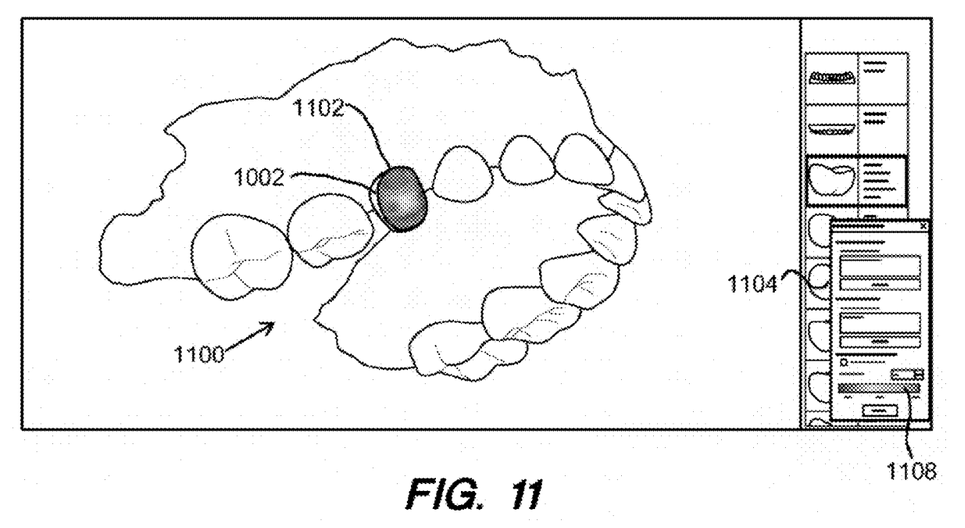
FIG. 11 is a digital image created by the present invention showing a superimposition of initial operator tooth preparation and required tooth reduction highlighting areas topographically in need of further reduction for crown fit.

As shown in FIG. 2, the user or a third party then prepares the tooth preparation 1000 based upon the digital preparation form. As shown in FIG. 2 and FIG. 10, a digital 3D representation is captured 1050 of the prepared tooth using the intraoral scanner 101 and the computing device 12. This digital 3D representation of the prepared tooth is compared to the planned digital tooth preparation form. The system is configured to compare the digital 3D representation of the prepared tooth to the planned digital tooth preparation form to determine and illustrate areas requiring further reduction, as illustrated in FIG. 11. This comparison can be performed using topographic overlay of the images or artificial intelligence. The user then can determine areas for further removal or tooth preparation prior to the final step of pediatric crown placement 1200. Once the crown is selected or placed, the system 10 has an automatic reordering tool configured to automatically reorder 1250 the selected crown to replenish the inventory.

Figure 3:
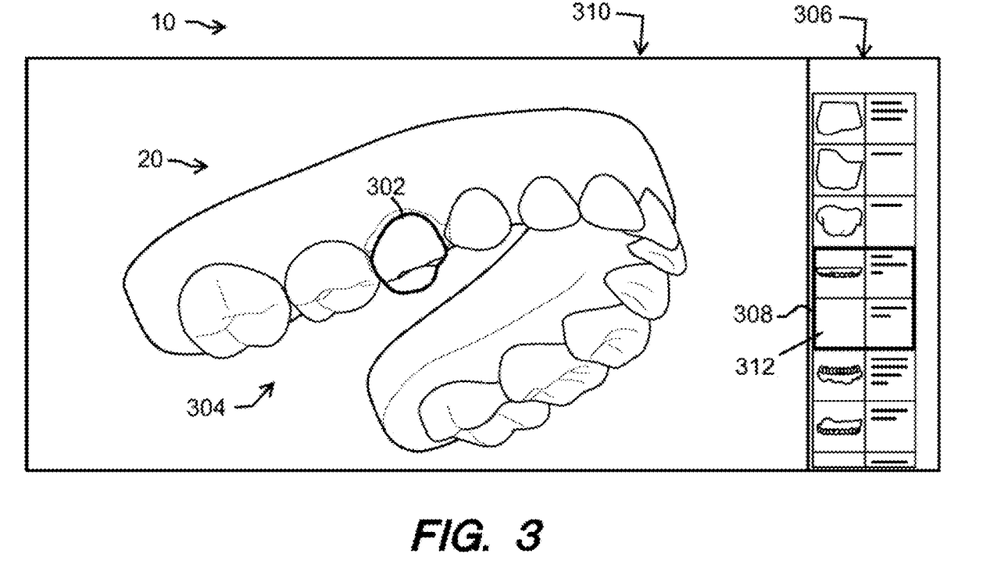
FIG. 3 is a digital image created by the present invention showing an affected tooth.
Figure 4:
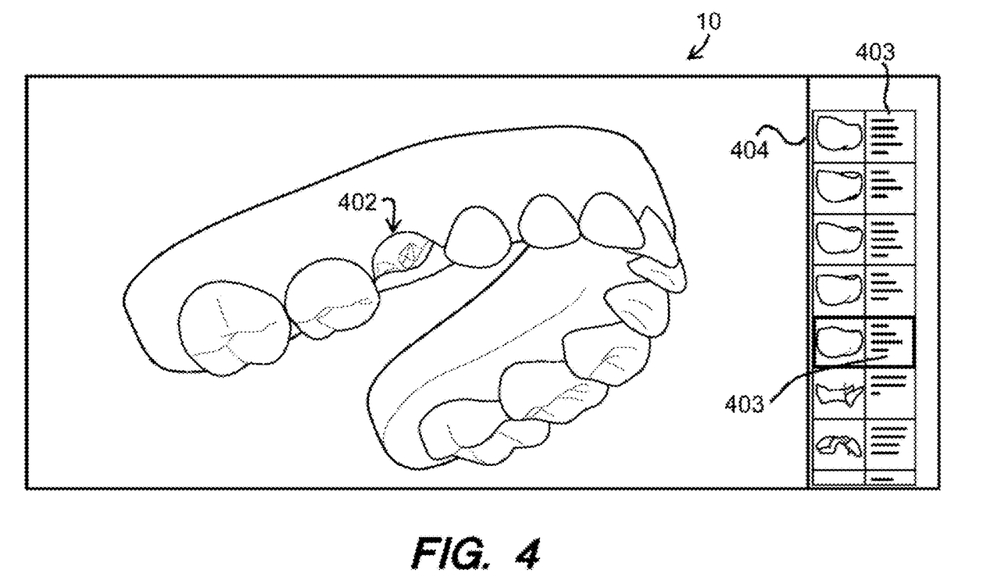
FIG. 4 is a digital image created by the present invention showing the affected tooth digitally extracted for restorative analysis.

FIG. 3 shows the user interface 310 of the present invention showing a menu 306 and digital image 20 of a three-dimensional representation of an affected tooth 302 created by the method of the present invention. As shown, the system 10 displayed on the computing device 12 through the user interface provides the digital image of the pediatric mouth with traditional 3D rendering tools to allow manipulation of the image, such as zooming or tilting. The interface includes a tool bar 306 to allow highlighting of the tooth 302 for preparation, as indicated by the bolded selections 308 on the tool bar 306, and digital removal of the tooth as further shown below. In particular, FIG. 3 shows the selection of the digital removal tool 312 on the menu which requests the platform provide a digital image of the three-dimensional representation of the teeth without the selected tooth 302. The tool 312 is then configured to analyze the digital open space of the absent tooth, including the size of the open space. Additional tools of the tool bar will be discussed further below.

FIG. 4 shows the user interface 310 of the present invention showing a menu and a digital image created by the present invention showing the affected tooth digitally removed to create an empty space 402 for analysis. As shown, the system 10 displayed on the computing device 12 through the user interface provides a menu 404 or inventory list of the potential pediatric crowns in a Match Inventory List. The potential pediatric crowns are described based on their characteristics, such as universal, midsize or fullsize, narrow or wide, and left, right or both. The user can then select a potential pediatric crown to digitally place in the space of the digitally removed tooth. As noted above, the potential pediatric crowns for selection may be selected through artificial intelligence or characteristics assigned to the potential pediatric crowns in the inventory database or file storage of the system 10.

FIG. 5 shows the user interface 310 of the present invention showing a menu and a digital image created by the present invention showing the digital placement of a potential crown drawn from the database system of the present invention demonstrating a resulting misfit because the virtual crown selected is too large. As shown, the user may digitally place a potential pediatric crown from the Match Inventory List into the space of the digitally removed tooth to determine fit with the space and the surrounding teeth. As shown, the potential pediatric crown 502 in this selection is too large for the space and the user can now successfully remove this potential pediatric crown from consideration.

FIG. 6 shows the user interface 310 of the present invention showing a menu and a digital image created by the present invention showing the virtual placement of a potential crown drawn from the database system of the present invention demonstrating a resulting misfit because the virtual crown 602 selected is too small. As shown, the user may digitally place a potential pediatric crown from the Match Inventory List into the space of the digitally removed tooth to determine fit with the space and the surrounding teeth. As shown, the potential pediatric crown in this selection is too small for the space and the user can now successfully remove this potential pediatric crown from consideration.

FIG. 7 shows the user interface 310 of the present invention showing a menu and a digital image created by the present invention showing the digital placement of a potential crown 702 drawn from the database system of the present invention demonstrating a good fit because the virtual crown dimensions are optimal. As shown, the user may digitally place a potential pediatric crown from the Match Inventory List 404 into the space of the digitally removed tooth to determine fit with the space and the surrounding teeth. As shown, the potential pediatric crown in this selection is an appropriate fit for the space and the user can now move towards considering the preparation of the tooth that is being replaced. As shown, the user interface of the system 10 provides a tooth preparation taskbar 710 that shows the necessary preparation 712 of the extrapolated tooth to match the interior of the selected crown as noted by the data on the selected crown 702 in the system file storage or database.

FIG. 8 shows the user interface 310 of the present invention showing a menu and a digital image created by the present invention showing a digital form 802 for the tooth preparation of the affected tooth extrapolated from the known interior dimensions of the optimal virtual crown. The digital tooth preparation 802 is based upon the characteristics of the interior of the selected pediatric crown. The use of the digital tooth preparation 802 as a guide allows the dentist to minimize time spent on tooth preparation while the pediatric dental patient is under anesthesia. As shown, the user interface of the system 10 provides a tooth preparation tool selection to automatically provide the appropriate tooth preparation plan based upon the selected pediatric crown.

FIG. 9 shows the user interface 310 of the present invention showing a menu and a digital image created by the present invention showing the affected tooth 302 contours superimposed on the tooth preparation form 802 required for fitting the optimal virtual crown. As shown, the user interface of the system 10 provides a test crown tool to superimpose the selected pediatric crown over the tooth form.

FIG. 10 shows the user interface 310 of the present invention showing a menu and a digital image created by the present invention showing an initial tooth preparation 1002 of the affected tooth. During the process of tooth preparation, the user may use the intraoral scanner 101 and the system 10 to prepare an intraoral image 1006 of the initial tooth preparation of the tooth for comparison to the tooth preparation plan 802 shown in FIG. 8. Additionally, the system may contain an artificial intelligence engine to aid in determining and/or identifying if the scanned intraoral image of the initial tooth preparation of the affected tooth does not meet the requirements of the system, namely if the intraoral digital image does not match the planned tooth preparation. The artificial intelligence engine may prompt the dentist immediately after the scan that more tooth material needs to be removed.

FIG. 11 shows the user interface 310 of the present invention showing a menu and a digital image created by the present invention showing an analysis 1102 of ideal tooth preparation form superimposed with the initial tooth preparation 1002 completed by the operator. Areas topographically in need of further reduction for optimal crown fit can be highlighted, color-mapped and/or quantified via computer software. As shown, the user interface of the present system 10 uses color to indicate areas that are close to tooth preparation plan. The system 10 provides the user with an analysis menu 1104 that includes a color bar 1108 to provide elaboration of the colors represented in the analysis form 1102 shown in the digital image 1100 In this manner, the dentist user can verify the tooth preparation will fit the pediatric crown interior virtually before any attempt to seat the selected crown physically, removing the potential for breaking the pediatric crown or harm to the patient (i.e. contamination, aspiration, pulpal damage, etc.) during placement of a pediatric crown that does not fit the tooth preparation.

Unless otherwise stated, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein. It will be apparent to those skilled in the art that many more modifications are possible without departing from the inventive concepts herein.

All terms used herein should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. When a Markush group or other grouping is used herein, all individual members of the group and all combinations and subcombinations possible of the group are intended to be individually included. All references cited herein are hereby incorporated by reference to the extent that there is no inconsistency with the disclosure of this specification. When a range is stated herein, the range is intended to include all sub-ranges within the range, as well as all individual points within the range. When "about," "approximately," or like terms are used herein, they are intended to include amounts, measurements, or the like that do not depart significantly from the expressly stated amount, measurement, or the like, such that the stated purpose of the apparatus or process is not lost.

The present invention has been described with reference to certain preferred and alternative embodiments that are intended to be exemplary only and not limiting to the full scope of the present invention, as set forth in the appended claims.

We claim:

1. A computerized system for treatment plan for pediatric crown surgery using a prefabricated crown replacement, the system comprising:
    a server having a memory storing an inventory database of multiple prefabricated crown replacements;
    a computing device having at least one processor and a display, the computing device configured to communicate with the server;
    an intraoral scanner in communication with the computing device;
    a platform in communication with the server and accessible via a network by the computing device, wherein the platform comprises:
        a user interface configured to receive and display a digital image of a three-dimensional representation of a patient's teeth as captured by the computerized system;
        a user interface tool configured to digitally remove a selected patient tooth to create an open space and digitally analyze the open space;
        an inventory menu displaying multiple prefabricated crown replacements from the inventory database for digital selection by the user;
        the user interface further configured to display an image of a digitally selected prefabricated crown replacement in the open space;
        a user interface tool configured to analyze the size and shape of the selected patient tooth and the interior size and interior shape of the digitally selected prefabricated crown replacement and prepare a digital tooth preparation form based on the analysis;
        the user interface further configured to display an image of a digital image of a three-dimensional representation of a patient's tooth preparation as captured by the computerized system prior to placement of the digitally selected prefabricated crown replacement; and
        a user interface tool configured to superimpose the patient's tooth preparation and the digital tooth preparation form during the patient's tooth preparation to provide topographical color analysis of areas on the patient's tooth preparation needing further reduction prior to placement of the selected prefabricated crown replacement.

2. The system of claim 1, the inventory database further including the characteristics of the multiple prefabricated crown replacements including size, image, tooth type, color, interior crown shape and interior crown size.

3. The system of claim 2, multiple prefabricated crown replacements displayed by the inventory menu further being selected from the inventory database based upon the characteristics of the multiple prefabricated crown replacements and the digital analysis of the open space.

4. The system of claim 1, further comprising an automatic reordering tool configured to reorder the digitally selected prefabricated crown replacement.

5. A computing device implemented method for providing a pediatric crown surgery using a prefabricated crown replacement, the computing device implemented method comprising:
    preparing a digital scan of a patient's teeth using an intraoral scanner configured to transmit digital image to a computing device;
    digitally identifying a selected patient tooth on the digital scan of the patient's teeth for a selected patient tooth for replacement;

determining parameters of the digital open space on the digital scan;

identifying for selection at least one prefabricated crown replacement from a stored inventory of prefabricated crown listings accessible by the computing device;

analyzing the size and shape of the selected patient tooth and the interior size and interior shape of the selected prefabricated crown replacement and preparing a digital tooth preparation form based on the analysis;

preparing a digital scan of a patient's tooth preparation using an intraoral scanner; and superimposing the digital tooth preparation form and the digital scan of the patient's tooth preparation during the patient's tooth preparation to provide a topographical color analysis of areas on the patient's tooth preparation needing further reduction prior to placement of the selected prefabricated crown replacement.

6. The method of claim 5, the at least one prefabricated crown replacement identified based upon the determined parameters of the selected patient tooth.

7. The method of claim 5, reordering the selected prefabricated crown replacement.

8. A platform in communication with a server and accessible via a network by a computing device for use in conjunction with pediatric crown surgery using a prefabricated crown replacement, the platform comprising:

a user interface configured to receive and display a digital image of a three-dimensional representation of a patient's teeth;

a user interface tool configured to digitally identify a selected patient tooth occupying a defined space and digitally analyze the defined space;

an inventory menu displaying multiple prefabricated crown replacements for digital selection by the user;

the user interface further configured to display an image of a digitally selected prefabricated crown replacement in the defined space;

a user interface tool configured to analyze the interior size and interior shape of the digitally selected prefabricated crown replacement and prepare a digital tooth preparation form based on the analysis;

the user interface further configured to display an image of a digital image of a three-dimensional representation of a patient's tooth preparation prior to placement of the digitally selected prefabricated crown replacement; and a user interface tool configured to provide topographical color analysis of areas on the patient's tooth preparation needing further reduction during the patient's tooth preparation and prior to placement of the selected prefabricated crown replacement.

9. The platform of claim 8, further comprising a user interface tool configured to analyze the size and shape of the selected patient tooth and the interior size and interior shape of the digitally selected prefabricated crown replacement and prepare a digital tooth preparation form based on the analysis.

10. The platform of claim 8, further comprising a user interface tool configured to superimpose the patient's tooth preparation and the digital tooth preparation form to provide topographical color analysis of areas on the patient's tooth preparation needing further reduction prior to placement of the selected prefabricated crown replacement.

11. The platform of claim 8, further comprising an automatic reordering tool configured to reorder the digitally selected prefabricated crown replacement.

* * * * *